United States Patent [19]

Adelman et al.

[11] Patent Number: 4,682,490

[45] Date of Patent: Jul. 28, 1987

[54] IMPACT TEST INSTRUMENT

[76] Inventors: Roger A. Adelman, 1562 Wittlou Pl., Cincinnati, Ohio 45224; David A. Corelli, 6527 Fountains Blvd., West Chester, Ohio 45069

[21] Appl. No.: 696,956

[22] Filed: Jan. 31, 1985

[51] Int. Cl.[4] .......................... G01N 3/30; G01M 7/00
[52] U.S. Cl. .......................................... 73/12; 73/662
[58] Field of Search ....................... 73/12, 82, 662, 579

[56] References Cited

U.S. PATENT DOCUMENTS

| 3,671,761 | 6/1972 | Shibuya et al. | 361/205 X |
| 4,333,019 | 6/1982 | Weigert | 361/205 X |
| 4,402,210 | 9/1983 | Vandeberg | 73/12 |
| 4,449,161 | 5/1984 | Kling | 361/205 X |
| 4,470,293 | 9/1984 | Redmon | 73/12 |
| 4,499,906 | 2/1985 | Wohlgemuth et al. | 73/82 X |
| 4,519,245 | 5/1985 | Evans | 73/579 |
| 4,542,639 | 9/1985 | Cawley et al. | 73/12 |

*Primary Examiner*—Charles A. Ruehl
*Attorney, Agent, or Firm*—Frost & Jacobs

[57] ABSTRACT

A power-actuated instrument for the impact excitation of mechanical structures includes means for producing a single impact force of variable magnitude and self-contained integrated electronic means for detecting, conditioning, and limit testing of the electronic representation of the impact force so delivered.

14 Claims, 4 Drawing Figures

IMPACT TEST INSTRUMENT

TECHNICAL FIELD

The present invention relates generally to structural testing and more particularly concerns an impact test instrument for exciting a mechanical structure with a broad range of vibratory motion for determining the mechanical resonances and vibration amplitudes of the structure. The invention will be specifically disclosed in connection with a hand held, power actuated impactor of variable and adjustable striking force having self-contained signal conditioning and processing instrumentation.

BACKGROUND OF THE INVENTION

In the past few years, it has proved to be socially and commercially advantageous to perform vibration testing and dynamic analysis on a wide range of mechanical structures. Such testing and analysis is conducted to determine the mechanical resonances and vibration amplitudes of structures in order to assure their functional stability. Knowledge of the mechanical resonances of a structure enhances the economic optimization of product design. Moreover, such knowledge enables the designer to avoid designs which are susceptible to vibrations at the structure's mechanical resonances. Structures which are so susceptible to vibrations at their mechanical resonances are not only subject to failure or malfunction, they may also pose safety problems. For example, vibrations reaching resonances in an automobile can cause severe road handling problems and passenger discomfort. As a further example, such resonance in an aircraft wing could cause the wing to flutter and to fail. Structural dynamic testing determines if such conditions exist, and permits the structure to be improved in ways to avoid harmful vibrations. In recent years such testing has been greatly enhanced by the use of computers employing mathematical algorithms and procedures, such as Fourier analysis. Such tools also enable the computer to graphically illustrate all of the structure's vibrational motions with an animated visual display.

In conducting such sophisticated tests, a structure is defined for the computer as a series of interconnected points, with each point representing an individual test point on the structure. It is not uncommon for more than a hundred test points to be so defined. At these points on the physical structure, either an excitation force is input, or a motion is detected. In any event, a pair of readings is always taken, an input force and an output motion between the test point and a reference point on the structure. The ratio of the time or frequency representations of the two signals constitute a "transfer function" between the two points. These transfer functions are the basis of the computer analysis and animation.

There are several ways to excite structures for such tests, each having its particular suitability. The two most popular classes of excitation are "shakers", hydraulically or electrically powered machines capable of producing various vibratory forces, and "impactors" which produce impulse forces. Shakers find utility where great amounts of energy must be imparted to a structure. In practice, shakers usually are placed at the reference point on the structure being tested. The companion motion sensor must then be mounted at each test point in order to establish a transfer function for that test point. Excitation of a broad band of vibratory motion is time consuming using shakers. Considerable time expenditure is required for both the placement of motion sensors and for driving the structure through a wide range of frequencies.

Testing with impactors on the other hand, requires substantially less energy and requires substantially less time and set-up costs. Additionally, impact testing inherently produces a broad frequency band of excitation. When testing is conducted using an impactor, the motion sensor is affixed to the reference point, and the impactor is used to simply strike each of the test points.

Prior art impactors have consisted of hammers and similar manual devices with which a sharp blow can be manually imparted to the structure. A force transducer is mounted on the striking surface of such hammers to generate an electrical signal representative of the impact force, which representative signal is processed by a signal acquisition system. A great deal of physical skill and dexterity is required in the use of the manual prior art devices to assure that a proper hit or impact is achieved. Missing the target point, hitting too hard or too softly, creating more than one impact on a single stroke are all errors that commonly occur until significant operator skill is developed. Furthermore, existing manual impact devices for this purpose require an external source of power for the transducer as well as external conditioning of the signals generated by the transducer. Often, this external signal conditioning occurs over long electrical leads. Since the determination of a valid signal is only accomplished at the computer, which is typically remote from the test structure, the long electrical leads represent a substantial source of electrical noise and error. Such prior art manual impact devices are also inherently restricted to environments which are not harmful to the operator. Further, such prior art devices are restricted to applications where there is adequate space for a hammer to be physically swung.

SUMMARY OF THE INVENTION

Accordingly, it is a primary object of the invention to provide an improved impact instrument for testing the structural dynamics of an object.

It is another object of the invention to provide an impact test instrument which may be employed by a low skilled operator in testing the structural dynamics of an object.

Yet another object of the invention is to provide an impact test instrument for imparting a controlled and consistently repeatable impact to a structure.

Still another object of the invention is to provide a structural testing instrument which may be readily positioned to impact a precise location on an object being tested.

Another object of the invention is to provide a structural testing instrument capable of exciting a structure with an impact of repeatable amplitude-time signature characteristics.

A still further object of the invention is to provide an instrument for impacting a structure with a force which may be continuously varied over a wide force range.

It is yet another object of the invention to provide an impact instrument having self contained, integrated instrumentation for structural testing.

Another object of the invention is to provide a structural impact test instrument which may be externally triggered in a hazardous or constrained environment to impart a precise and consistently repeatable impact.

A still further object of the invention is to provide an impact test instrument for accommodating a widely different range of structural compliances in objects being tested.

Another object of the invention is to provide a structural impact test instrument having means for optimizing both the mechanical interface with a structure being tested and for having independent means for optimizing the resulting electronic signal to the host data acquisition equipment.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved impact test instrument is provided for structural testing. The instrument includes a housing with a movable means at least partially disposed in the housing for imparting a controlled and repeatable impact to a stationary external structure. The movable means includes a force transducer for detecting the amplitude-time signature characteristics of the impact between the movable means and the external structure. Pulse means are also provided for triggering the movement of the movable means to initiate impact with the external structure. In accordance with one aspect of the invention, the pulse means provides an isolated pulse having a maximum predetermined repetition rate. In this way, a consistently repeatable isolated impact can be imparted to a repeatably precise location on the external structure.

In accordance with another aspect of the invention, the movable means includes a solenoid coil with an armature slidably movable along the solenoid coil axis. The armature is moved under the influence of a magnetic field generated by the solenoid coil.

In another aspect of the invention, the armature includes an internally threaded driving cylinder of nonmagnetic material. A core of magnetic material having external threads is internally disposed within the driving cylinder and threadably received thereby. Means are also provided for rotating the core relative to the driving cylinder to axially vary the position of the core within the driving cylinder.

In a further aspect of the invention, means are provided for resiliently biasing the driving cylinder to a predetermined axial position in the solenoid coil. The magnetic field generated by the solenoid coil applies an accelerating force to the core for moving said driving cylinder against the force of the biasing means. The magnitude of this accelerating force is dependent upon the relative axial position of the core within the driving cylinder.

In yet another aspect of the invention, the core rotating means includes an adjustment rod which extends through the bore of the core along the longitudinal axis of said driving cylinder. The adjustment rod and the bore have matching non-circular configurations to permit the core to freely slide longitudinally on the adjustment rod while simultaneously prohibiting relative rotational movement between these two elements.

In one specific aspect of the invention, a manually operative adjustment device is disposed outside the housing. The adjustment device is interconnected to the adjustment rod for common rotational movement therewith.

In a further aspect of the invention, the force transducer is firmly secured to the front axial end of said driving cylinder. A first bearing is preferably provided for slidably supporting the driving cylinder, while a second bearing is preferably provided for rotatably supporting the adjustment rod.

Another feature of the invention includes a handle portion of the housing for grasping the instrument and having a trigger optimally placed for manual activation. The handle portion preferably extends substantially perpendicular to the longitudinal direction of the driving cylinder and is used to house portions of an integrated electronic system.

Another specific aspect of the invention includes an anti-rattle spring disposed in the driving cylinder about the adjustment rod. The anti-rattle spring is used to axially urge the core toward a predetermined direction in the driving cylinder.

In another feature of the invention, means are also provided for limiting the output of the pulse means to a single pulse in response to a single trigger input, which input may be effected by either a manual input or a remote switch closure.

Still other objects of the present invention will become readily apparent to those skilled in this art from the following description wherein there is shown and described a preferred embodiment of this invention, simply by way of illustration of one of the best modes contemplated for carrying out the invention. As it will be realized, the invention is capable of other different embodiments, and its several details are capable of modifications in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification, illustrate several aspects of the present invention, and together with the description serve to explain the principles of the invention. In the drawings.

Reference will now be made in detail to the present preferred embodiment of the invention, an example of which is illustrated in the accompanying drawings.

DETAILED DESCRIPTION OF THE PREFERRED EMBODIMENT

Figure 1:
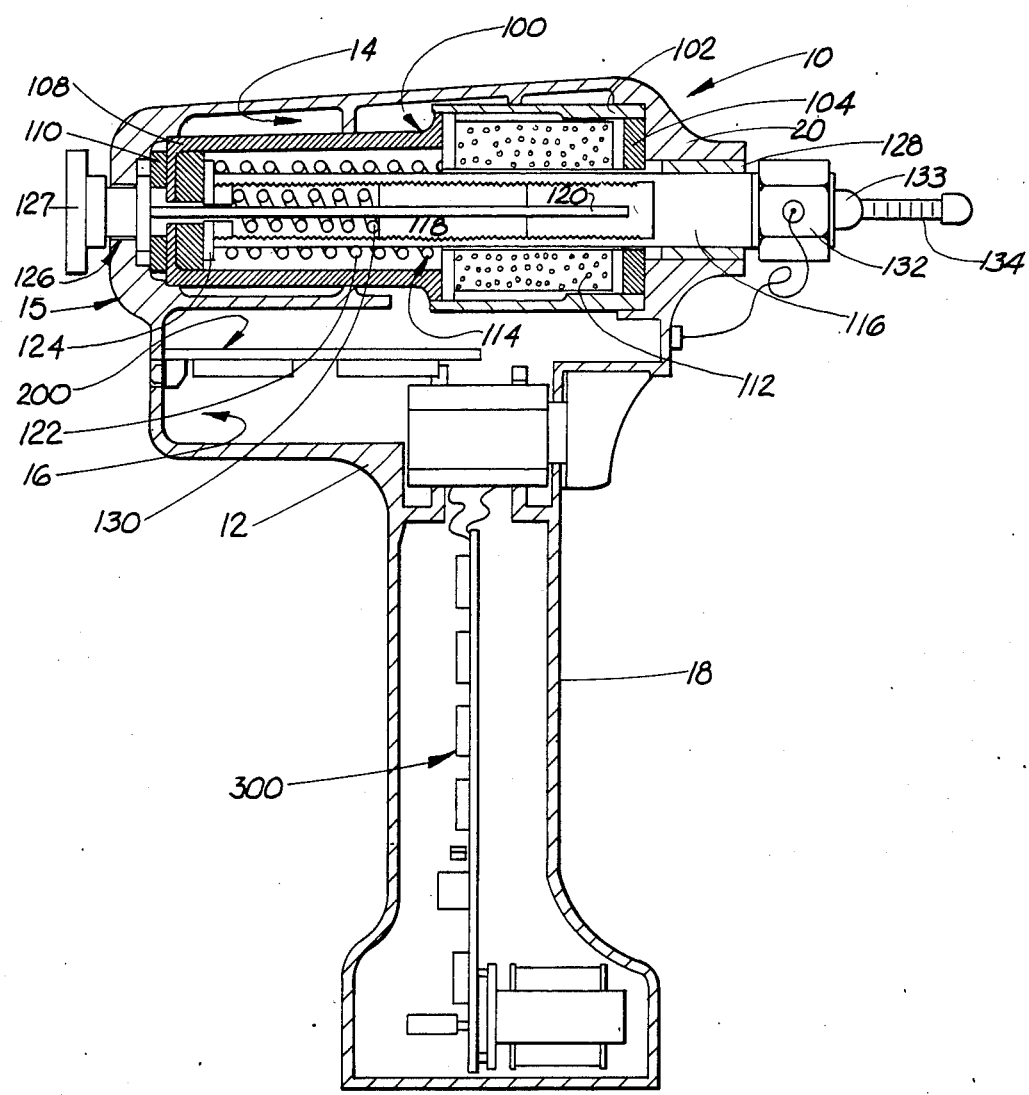
FIG. 1 is an elevational view, partially in cross-section, of a hand held impact instrument constructed in accordance with the principles of the present invention.

Referring now to the drawings, FIG. 1 is a partial cross-sectional elevational view of an impact instrument, generally designated by the numeral 10, constructed in accordance with the principles of the present invention for exciting a structure with an impact having a predetermined amplitude-time signature. The illustrated impact instrument 10 includes a housing 12 having a main body portion 15 comprised of first and second longitudinal housing chambers 14 and 16. The housing chambers 14 and 16 respectively enclose an impact motor assembly 100 and a signal and detection circuit assembly 200. A longitudinal handle portion 18 of the housing 12 extends downwardly from the main body portion 15 and perpendicularly joins the main body portion 15 at a lower intermediate portion of the second housing chamber 16. The handle portion 18 of the preferred embodiment encloses a trigger and power supply assembly, which trigger and power supply assembly is generally designated by the numeral 300 in FIG. 1.

The illustrated motor assembly 100 includes a solenoid housing 102 of generally cylindrical configuration. As shown in FIG. 1, the illustrated solenoid housing is positioned at the front axial end of the housing chamber 14 for maintaining a concentric relation between a power solenoid 112 with the housing 10. A compression bumper 104 is compressingly interposed between the outboard axial end of the solenoid housing 102 and a boss 20 on the front axial side of the housing chamber 14. The compression bumper 104 is resilient and provides the necessary force for maintaining the desired axial spatial relationship of the motor assembly 100 within the housing 10. The compression bumper 104 further functions to absorb energy and attenuate vibrations of the motor assembly 100 relative to the housing 12. A take-up housing 108 extends between the inboard axial end of the solenoid housing 102 and the rear axial side of the housing chamber 14. An assembly shim 110 is disposed between the take-up housing 108 and the rear axial side of the housing chamber 14 for urging the solenoid housing 102 against the resilient bumper 104.

The power solenoid 112 is disposed within the solenoid housing 102. The solenoid 112 defines an annulus through which an armature 114 is slidably movable. The armature is formed of a non-magnetic material, and in the preferred embodiment is assembled from a hollow non-magnetic stainless steel driver cylinder 116 with an end cap 124.

The driver cylinder 116 is internally threaded and contains a core 118 of magnetic material having external threads, which external threads are matchingly received by the internal threads of the driver cylinder 116. As will be readily apparent to those skilled in the art from this arrangement, rotational movement of the core 118 relative to the driver cylinder 116 is operative to axially advance the core 118 within the driver cylinder 116. In the illustrated embodiment, such relative rotational movement is effectuated by an adjustment rod 120 which extends along the longitudinal axis of the driver cylinder 116 and through a bore of non-circular cross-section in the core 118. The matching non-circular cross-sectional configurations permit the core 118 to be rotated for variable advancement within the driver cylinder 116 while permitting its unrestricted longitudinal movement on the adjustment rod 120. The adjustment rod 120 extends through the axial end cap 124 to a rear bearing assembly 126 which supports the adjustment rod 120 at the rear of the housing chamber 14. A manual adjustment device, such as a hand knob 127 is positioned outside the housing 12 and firmly attached to the rear bearing assembly 126. Rotation of the hand knob 127 rotates the adjustment rod 120, which in turn, rotates the core 118 relative to the driver cylinder 116. Thus, the longitudinal positioning of the core 118 within the driver cylinder 116 is readily effectuated by rotating the external hand knob 127.

The front axial end of the driver cylinder 116 is slidably movable in a front bearing 128 positioned on the forward side of the compression bumper 104. The front bearing 128 supports the front end of the driver cylinder 116. A piezoelectric force transducer 132 is affixed to and supported by the front axial end of the driver cylinder 116 for common movement therewith. An impact tip 133 of selected resilience and compliance is supported by the forward end of the transducer 132. A compression spring 122 extends between the solenoid housing 102 and the cylinder end cap 124 in circumferential relationship to the driver cylinder 116 for urging the driver cylinder 116 toward this rearward most position, as depicted in FIG. 1. An anti-rattle spring 130 is also disposed within the driver cylinder 116 between the core 118 and the rearmost axial end of cylinder 116. The anti-rattle spring 130 maintains a pressure against the core 118 to minimize relative axial movement between the contacting surfaces of the internal and external threads of the driver cylinder 116 and the core 118 respectively.

The forward end of the housing 12 also preferably includes a pair of columnar spacing members 134 disposed in spaced parallel relationship to the force transducer 132. The spacing members are used to engage the structure to be tested alongside the desired impact location and to axially space the force transducer 132 (and impact tip 133) from that desired impact location.

The second housing chamber 16 is positioned immediately beneath the first housing chamber 14 and, as noted above, encloses the signal and detection circuit assembly 200, which in the preferred embodiment is configured on a printed circuit board. In general, the signal processing and detection circuitry 200 is used to sense the force imparted to a structure being tested by the piezoelectric force transducer 132.

Figure 2:
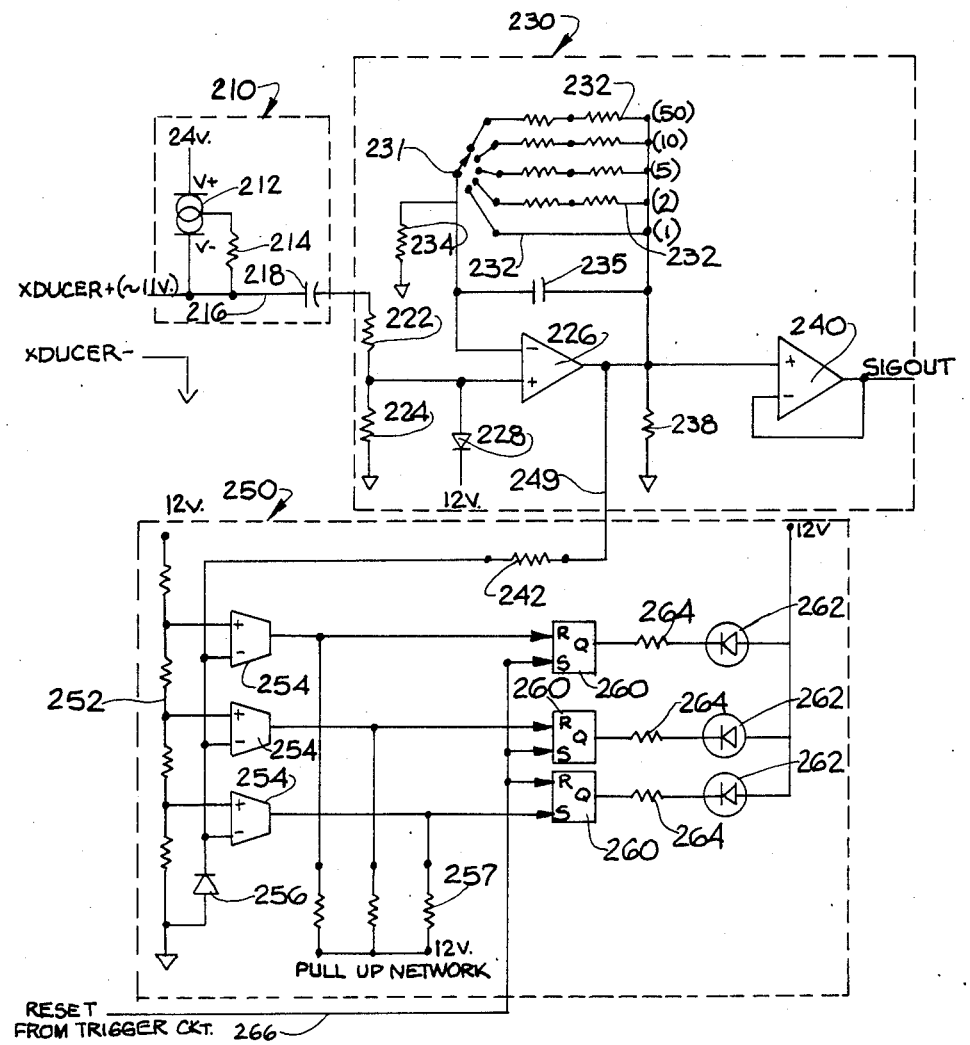
FIG. 2 is a schematic representation of a signal processing and detection circuit for preconditioning a supply signal to a transducer in FIG. 1 for acquiring an output signal from the transducer to amplify that signal and indicating when that signal has exceeded predetermined limits.

With specific reference to FIG. 2, a schematic representation of the preferred signal and detection circuit assembly 200 is illustrated. A combined constant current source and voltage conversion circuit 210 provides the electrical conditioning for the integrated circuit-piezoelectric force transducer 132. A programmable constant-current diode 212 is adjusted with regulating resistor 214 to provide a constant current along a circuit pathway 216 to force transducer 132 (FIG. 1). The force transducer 132 provides a current drain on electrical pathway 216 proportional to the force applied by the transducer 132, causing the voltage on electrical pathway 216 to vary sympathetically. A coupling capacitor 218 permits only AC voltage signals to be communicated between the circuit 210 and an amplifier circuit 230.

Continuing with FIG. 2, the illustrated amplifier circuit 230 provide a voltage includes a pair of resistors 222 and 224 for dividing the signal voltage and in cooperation with the capacitor 218 for setting the time constant of the circuit. As so configured, the resistors 222 and 224 limit the input voltage to the amplifier 226 below its supply values. A trap diode 228 further assures signal voltage limitation to the amplifier input. The gain of amplifier 226 is selected by the position of a switch 231 which communicates one of a plurality of parallel feedback resistor paths 232 to the junction of a reference resistor 234 to form a voltage divider circuit at the negative input of the amplifier 226. A feedback capacitor 235 limits very high frequency response and minimizes electrical noise in the amplifier 226.

A load resistor 238 is interposed between the output of amplifier 226 and a voltage follower amplifier 240 to provide protection between the external instrumentation and sensitive portions of the signal conditioning circuitry 230. At this same location between the two amplifiers 226 and 240, an electrical pathway 249 at this same location is provided to communicate the output signal of the amplifier 226 to a detection and enuciator circuit 250. A current limiting resistor 242 is disposed in this communication path 249.

The detection portion of circuit 250 consists of a voltage divider network 252 to provide reference voltages for a plurality of voltage comparators 254. A trap diode 256 is provided on the signal voltage line to protect the comparators 254. Each of the outputs of the comparators 254 are held in a high state by a pull-up network 257 except when the input signal exceeds the reference voltage on any comparator. The outputs of the comparators thus provide a two-state signals on each line which are, in turn, communicated to the input terminals of a plurality of corresponding set-reset flip-flops 260. The flip-flops together with the light emitting diodes 262 and current limiting resistors 264 comprise an enuciator which will remain lighted on detection upon exceeding predetermined limits of a fault and will remain lighted until a reset signal is received from the trigger network 350 of FIG. 3 on electrical pathway 266.

Figure 3:
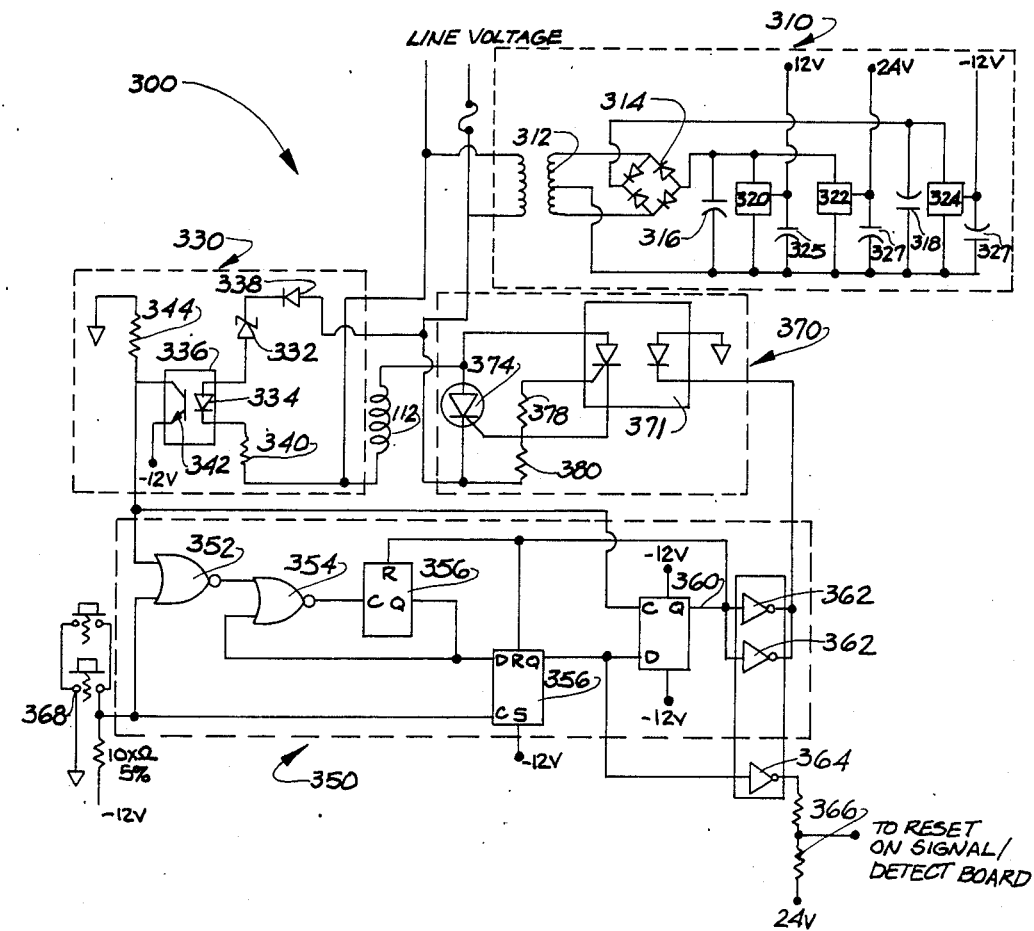
FIG. 3 is a schematic representation of a power supply for energizing the impact motor of FIG. 1 and a logic and trigger circuit used to support the electronics of FIG. 2.

Turning now to FIG. 3, it is seen that the power supply, logic and trigger circuit 300 includes a clock 330, a trigger logic network 350, a power switching network 370, and a triple voltage linear regulated power supply 310. The clock 330 derives a logic voltage level pulse train from the AC line voltage. This AC line voltage is passed through a zener diode 332 of sufficient breakdown voltage to only conduct the top 20 to 30 volts of the AC line voltage. A light emitting diode 334 of optocoupler 336 is activated by current conducted through the zener diode 332. A reverse blocking diode 338 and a resistor 340 provide voltage and current protection for this electrical pathway. A phototransistor 342 of the optocoupler 336 conducts in response to the illumination of light emitting diode 334 causing the voltage at the junction of the resistor 344 and the collector of transistor 342 to drop to a low state.

The output of clock 330 is communicated to the trigger logic network 350. A first NOR gate 352 combines the inputs of the clock 330 and the trigger switch 368 to provide one input to a second NOR gate 354. The output of NOR gate 354 drives a ripple counter 356. The other input to the second NOR gate 354 is derived from the output of the ripple counter 356 and causes clocking of the ripple counter 356 to cease after a predetermined number of clock cycles. The output of the ripple counter 356 is also directed to the data terminal of a D flip-flop 358. The clock terminal of this flip-flop is in communication with a series of parallel switches 368, the closure of any of which initiates a triggering of a single power pulse corresponding to a half wave of the AC line voltage. On such a swtch closure, the state on flip-flop 358 is moved to the output which is in communication with the data terminal of a second D flip-flop 360. The clock terminal of this second D flip-flop is driven by the clock 330, and moves the data state to the output of flip-flop 360. This output is communicated to a buffer inverter 362 and also to the reset lines of the first flip-flop 358 and the ripple counter 356. Yet another output path exists from the first flip flop 358 to the buffer inverter 364, the output of which is tied to one end of a voltage divider pair of resistors 366. The center tap of this voltage divider serves as a reset signal for an enuciator circuit 260.

The power switching network 370 consists of an optocoupled SCR 371 which fires in response to the logic output of buffer 362, and a power SCR 374 which permits current to flow through the solenoid 112 (also shown in FIG. 1). Current bleed resistors 378 and 380 avoid voltage build up on the SCR gates.

The linear triple power supply 310 producing nominal +24 volts, +12 volts, and −12 volts utilizes a center tap transformer 312, a diode full wave rectifier 314, storage capacitors 316 and 318, and integrated circuit linear voltage regulators 320, 322, and 324. Ripple capacitors 325, 327, and 329 are placed between the regulated voltage lines and ground to minimize high frequency noise on the regulated voltages.

Figure 4:
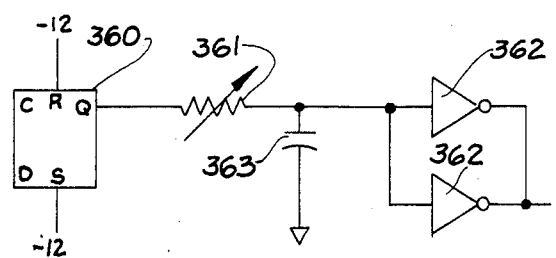
FIG. 4 is a schematic depiction of a means for variably delaying the initiation of a signal to fire the SCR trigger element of FIG. 3.

An alternative circuit as shown schematically in FIG. 4 may be interposed between elements 360 and 362 of FIG. 3 to effect further electrical control over the impactive force produced by solenoid 112. A variable resistor 361 is used to selectively charge capacitor 363 to effectively delay the presentation of a logical high voltage to buffer invertor 362. Such delay causes the firing of the solenoid 112 to occur over a reduced portion of the AC line power half-cycle.

In summary, numerous benefits have been described which result from employing the concepts of the invention. The impact instrument 10 is readily positioned adjacent a desired impact location on a structure to be tested, the distance of the instrument 10 being positioned by the columnar spacing members 134. An impact is initiated by the closure of a trigger switch, such as a manual trigger, causing a single pulse of the impact motor to be delivered through the force transducer to the structure. In response to the impact, an electrical signal is generated and amplified in self contained integrated circuitry disposed in the instrument housing. Limit detection of the signal occurs and an appropriate enuciation of the limit conditions is provided by instrument mounted LED's. If improper signal voltage is obtained or if the mechanical impact is deemed to be improper, appropriate adjustments to electrical or mechanical controls can be readily made on the impact instrument itself. The time amplitude signature produced by the structural response of the test object is provided for direct acquisition and analysis by complementary data analyzing electronic equipment.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

We claim:

1. An impact test instrument for structural testing, comprising:
   (a) a housing;
   (b) movable means at least partially disposed in said housing for imparting a controlled and repeatable impact to an external structure whose position is stationary relative to said housing, said movable means including a force transducer for detecting the amplitude-time signature characteristics of the impact between the movable means and the external structure; and
   (c) pulse means responsive to an a.c. electrical source for triggering the movement of said movable means and initiating impact between said movable means and the external structure, said pulse means being adjustable to vary the total electrical energy of the application of a half wave of the a.c. power source to the movable means, said pulse means providing an isolated pulse having a maximum predetermined repetition rate whereby isolated impact can be imparted to a repeatedly precise location on said external structure.

2. An impact test instrument as recited in claim 1 wherein said movable means includes a solenoid coil with an armature slidably movable along the solenoid coil axis under the influence of a magnetic field generated by said solenoid coil in response to a continuously and variably determinable portion of an a.c. signal from said electrical source, such electrical triggering and controlling means being completely isolated from such power circuit by optoelectronic devices.

3. An impact test instrument as recited in claim 2 wherein said armature includes an internally threaded driver cylinder of non-magnetic material, a magnetic core adjustably disposed within said driver cylinder, said core having external threads received by the internal threads of the driver cylinder, and means for rotating said core relative to said driver cylinder to axially vary the position of the core within said driver cylinder.

4. An impact test instrument as recited in claim 3 further including means for resiliently biasing said driver cylinder to a predetermined axial position with respect to said solenoid coil, the magnetic field generated by the solenoid coil applying an accelerating force to said core for moving said driver cylinder against the force of the biasing means, the magnitude of the accelerating force being dependent upon the relative axial position of said core within said driver cylinder.

5. An impact test instrument as recited in claim 4 wherein said core rotating means includes an adjustment rod extending through a bore of said core along the longitudinal axis of said driver cylinder, said adjustment rod and bore having matching non-circular configurations to permit the core to freely slide longitudinally on the adjustment rod while simultaneously prohibiting relative rotational movement between the core and the adjustment rod.

6. An impact test instrument as recited in claim 5 further including a manually operative adjustment knob disposed outside said housing, said adjustment knob being interconnected to said adjustment rod for common rotational movement therewith.

7. An impact test instrument as recited in claim 6 wherein said force transducer is firmly secured to the front axial end of said driver cylinder.

8. An impact test instrument as recited in claim 7 further including a bearing for slidably supporting said driver cylinder.

9. An impact instrument as recited in claim 8 further including a bearing for rotatably supporting said adjustment rod.

10. An impact instrument as recited in claim 9 wherein said housing includes a handle portion for manually grasping the instrument, said handle portion extending substantially perpendicular to the longitudinal direction of the driver cylinder.

11. An impact instrument as recited in claim 10 further including an anti-rattle spring disposed in said driver cylinder about said adjustment rod, said anti-rattle spring axially urging said core toward a predetermined position in said driver cylinder.

12. An impact instrument as recited in claim 10 further including a manual trigger positioned adjacent said handle portion of said housing, movement of said manual trigger being operative to activate said pulse means.

13. An impact instrument as recited in claim 12 further including means for limiting the output of the pulse means to a single pulse in response to a single movement of the manual trigger.

14. An impact instrument as recited in claim 3 wherein the force transducer is a piezoelectric force transducer.

* * * * *